US011958881B2

(12) United States Patent
Lin et al.

(10) Patent No.: US 11,958,881 B2
(45) Date of Patent: Apr. 16, 2024

(54) OPTIMIZATION METHOD FOR CAPTURING PROTEINS BY MULTI-COLUMN CONTINUOUS CHROMATOGRAPHY (MCC)

(71) Applicant: ZHEJIANG UNIVERSITY, Hangzhou (CN)

(72) Inventors: Dongqiang Lin, Hangzhou (CN); Ce Shi, Hangzhou (CN); Shanjing Yao, Hangzhou (CN)

(73) Assignee: ZHEJIANG UNIVERSITY, Hangzhou (CN)

( * ) Notice: Subject to any disclaimer, the term of this patent is extended or adjusted under 35 U.S.C. 154(b) by 0 days.

(21) Appl. No.: 18/117,479

(22) Filed: Mar. 6, 2023

(65) Prior Publication Data

US 2023/0203092 A1 Jun. 29, 2023

Related U.S. Application Data

(63) Continuation of application No. PCT/CN2021/122735, filed on Oct. 9, 2021.

(30) Foreign Application Priority Data

Nov. 10, 2020 (CN) .......................... 202011245944.7

(51) Int. Cl.
*B01D 15/18* (2006.01)
*B01D 15/08* (2006.01)
*C07K 1/20* (2006.01)

(52) U.S. Cl.
CPC ............ *C07K 1/20* (2013.01); *B01D 15/1871* (2013.01)

(58) Field of Classification Search
None
See application file for complete search history.

(56) References Cited

U.S. PATENT DOCUMENTS

| | | | |
|---|---|---|---|
| 7,901,581 B2 | 3/2011 | Bryntesson et al. | |
| 2014/0299547 A1 | 10/2014 | Muller-Spath et al. | |
| 2017/0016864 A1* | 1/2017 | Gjoka ............... | B01D 15/1864 |
| 2018/0001227 A1 | 1/2018 | Hilgert | |
| 2018/0236377 A1 | 8/2018 | Stone | |
| 2019/0374876 A1 | 12/2019 | Hilgert | |

FOREIGN PATENT DOCUMENTS

| | | |
|---|---|---|
| CN | 103884816 A | 6/2014 |
| CN | 106914222 A | 7/2017 |
| CN | 109473143 A | 3/2019 |
| CN | 109475789 A | 3/2019 |
| CN | 110348089 A | 10/2019 |
| CN | 111068360 A | 4/2020 |
| CN | 112451996 A | 3/2021 |
| EP | 0770869 A2 | 5/1997 |
| IN | 107064340 A | 8/2017 |

OTHER PUBLICATIONS

Mengting Li, et al., Development and application of hydrophobic charge-induction chromatography for bioseparation, Journal of Chromatography B, 2019, pp. 1-8, vol. 1134-1135, 121850.

Gao Zong-Ye, et al., Process design and application of twin-col. continuous chromatography for antibody affinity separation, Journal of Chemical Engineering of Chinese Universities, 2019, pp. 117-127, vol. 33, No. 1.

Ce Shi, et al., Model-based process development of continuous chromatography for antibody capture: A case study with twin-column system, Journal of Chromatography A, 2020, pp. 1-11, vol. 1619, 460936.

Rahul Godawat, et al., Periodic counter-current chromatography—design and operational considerations for integrated and continuous purification of proteins, Biotechnology Journal, 2012, pp. 1496-1508, vol. 7, No. 12.

* cited by examiner

*Primary Examiner* — Daniel E Kolker
*Assistant Examiner* — James L Rogers
(74) *Attorney, Agent, or Firm* — Bayramoglu Law Offices LLC

(57) ABSTRACT

An optimization method for capturing proteins by multi-column continuous chromatography (MCC), including the following steps: step 1, under the conditions of a set loading protein concentration and an arbitrary load residence time, performing a single time of protein breakthrough experiment to obtain a protein breakthrough curve; step 2, under a set breakthrough percentage for a target protein, integrating the breakthrough curve to obtain a single-column loading capacity and establishing a linear relationship between the inter-connected load time and the load residence time; step 3, solving for the optimal number of operating columns for capturing proteins by MCC based on step 2; step 4, solving for the optimal load residence time for capturing proteins by MCC based on step 2, step 3; and step 5, solving for the maximum productivity of capturing proteins by MCC based on step 4.

5 Claims, 6 Drawing Sheets

OPTIMIZATION METHOD FOR CAPTURING PROTEINS BY MULTI-COLUMN CONTINUOUS CHROMATOGRAPHY (MCC)

CROSS REFERENCE TO THE RELATED APPLICATIONS

This application is a continuation application of International Application No. PCT/CN2021/122735, filed on Oct. 9, 2021, which is based upon and claims priority to Chinese Patent Application No. 202011245944.7, filed on Nov. 10, 2020; the entire contents of which are incorporated herein by reference.

TECHNICAL FIELD

The present invention relates to a protein chromatographic separation technology in the fields of biochemical engineering and bioengineering, particularly to an optimization method for capturing proteins by multi-column continuous chromatography (MCC).

BACKGROUND

Monoclonal antibodies (mAbs) are the most important biotechnological drugs and have the characteristics of good targeting, high efficacy, and few toxic side effects. In recent years, with the growth of upstream cell expression and the expansion of production scale, more and more attention has been paid to the productivity and economy of downstream separation and purification processes. The separation of mAbs is traditionally achieved by three-step single-column batch chromatography based on protein A affinity capture, the process of which is less efficient and can hardly keep pace with the rapidly growing upstream process. The protein A affinity resin is also expensive. Therefore, it is very important to improve the productivity of mAb capture process and the capacity utilization of the protein A affinity resin.

In recent years, a new continuous chromatography technology, i.e., multi-column periodic counter-current chromatography (MPCC), has been successfully applied to the protein A affinity capture process of antibodies. The core of the continuous chromatography is two-column loading in series. The breakthrough protein from the first column is captured by the second column. The first column stops loading when a set protein breakthrough percentage is reached, and the loading switches to the second column. The first column is then eluted and regenerated, and multiple columns are alternated to achieve continuous chromatographic separation, thereby improving productivity, resin capacity utilization, reducing buffer consumption and equipment size. The patent US 007901581 B2 proposes a method of three-column continuous chromatography and is applied to capturing mAbs in mammalian cell culture supernatants. The patent US 2017/0016864 A1 proposes a method of MCC for protein capture, which optimizes the operation mode and productivity of the continuous chromatography process through multiple protein breakthrough experiments with different load residence times. Godawat et al. (Biotechnol. J, 7:1496-1508, 2012) proposed that the error function could be used to fit the breakthrough curve to obtain the dynamic binding capacity for the design of the MCC process. However, this method can only optimize the process for single load residence time. If the load residence time changes, the protein breakthrough experiments and fitting should be re-performed.

When MPCC is used for protein capture and the number of chromatographic columns is greater than or equal to 3, the specific operation mode is shown in FIG. 1 (three-column mode) and FIG. 2 (four-column mode). For the three-column mode shown in FIG. 1, chromatographic columns #1 and #2 are connected in series for loading, and chromatographic column #3 is eluted and subjected to the recovery and regeneration (R-R) step (Step 1). When column #3 is completely eluted and regenerated, column #1 also reaches the set protein breakthrough percentage. Columns #1 and #3 are connected in series, and the unadsorbed protein in column #1 is washed to column #3. At the same time, the feed is switched to column #2, and the sample is loaded at a constant speed (Step 2). After column #1 is completely washed, column #1 is disconnected from column #3, and column #2 is connected to column #3 for continuous loading, while column #1 is subjected to the R-R Step (Step 3). When column #1 is completely eluted and regenerated, column #2 also reaches the set protein breakthrough percentage. Column #2 and column #1 are connected in series, and the unadsorbed protein in column #2 is washed to column #1. At the same time, the feed is switched to column #3, and the sample is loaded at a constant speed (Step 4). After column #2 is completely washed, column #2 is disconnected from column #1, and column #3 is connected to column #1 for continuous loading, while column #2 is subjected to the R-R Step (Step 5). When column #2 is completely eluted and regenerated, column #3 also reaches the set protein breakthrough percentage. Column #3 and column #2 are connected in series, and the unadsorbed protein in column #3 is washed to column #2. At the same time, the feed is switched to column #1, and the sample is loaded at a constant speed (Step 6). From Step 1 to Step 6, each column has completed all the steps of a chromatographic separation operation and returned to the initial state, that is, a cycle has been completed. Repeating the above steps can achieve three-column continuous chromatography.

The four-column mode is similar to the three-column mode, as shown in FIG. 2. Similarly, two columns are connected in series for loading, but the R-R Step is divided into two stages which are carried out in two columns simultaneously. From Step 1 to Step 8, a separation cycle is completed. Repeating the above steps can achieve four-column continuous chromatography. The three-column and four-column modes can be further extended to N-column continuous chromatography. Similarly, two columns are connected in series for loading, but the R-R step is divided into (N-2) stages which are carried out in (N-2) chromatographic columns simultaneously. In the above continuous chromatography, the loading is generally conducted at the same flow rate throughout the whole process, so the operating time of each step needs to be reasonably matched. For three-column continuous chromatography, Step 1, Step 3, and Step 5 need to match the interconnected load time $t_C$ with the R-R time $t_{RR}$. For four-column continuous chromatography, Step 1, Step 3, Step 5, and Step 7 need to match the interconnected load time $t_C$ with the R-R time $t_{RR1}$ and $t_{RR2}$. If the two do not match, the faster step has to wait for the slower step to complete, resulting in decreased productivity. If the two are matched, that is, the two times are equal, then the MCC can achieve maximum productivity. $t_{RR}$ and $t_{CW}$ are usually determined by the optimization of washing, elution and regeneration processes with single-column batch chromatography, while $t_C$ is associated with a plurality of factors, such as the operation mode of continuous chromatography, the residence time of interconnected load process, the set protein breakthrough percentage, and the like. Because the MCC process is complex and many parameters need to be investigated, conducting screening and optimization only through experiments may lead to an extremely large workload. Establishing mathematical models for rational process characterization and auxiliary design can significantly improve the efficiency of process optimization and reduce the experimental workload. Shi et al. (J. Chromatogr. A., 1619:460936, 2020) adopt a general rate model with parallel diffusion to describe the breakthrough curve, which optimizes the productivity and resin capacity utilization of the twin-column continuous chromatography and achieves good results. However, the optimization with the help of the mechanism model requires that a system of partial differential equations be solved, which takes long time and has high requirements for personnel, so it is quite difficult in practical application. Therefore, it is very necessary to develop a simpler and more efficient method to assist in the optimization of the continuous chromatography process.

Aiming at the complexity of MCC process optimization, reducing the blindness of experimental screening and the difficulty in mechanism model optimization and to improve the efficiency of process development, the present invention proposes a new optimization method for capturing proteins by MCC. Based on a large number of experiments and systematic model analysis, it was found that there is a linear relationship between the interconnected load time and the load residence time under certain conditions. Based on the linear relationship, the number of operating columns, the optimal load residence time, and the maximum productivity of MCC can be obtained quickly through a single protein breakthrough experiment and simple calculation.

SUMMARY

Given the above technical problems, the present invention provides an optimization method for capturing proteins by MCC, which aims at simply and quickly optimizing operation modes and operation parameters of the MCC.

To solve the above technical problems, the present invention adopts the following technical solution:

An optimization method for capturing proteins by MCC, including the following steps:

Step 1, under the conditions of a set loading protein concentration and an arbitrary load residence time, performing a single time of protein breakthrough experiment to obtain a protein breakthrough curve;

Step 2, under a set breakthrough percentage (greater than or equal to 50%), integrating the breakthrough curve to obtain a single-column loading capacity of continuous chromatography and establishing a linear relationship between the interconnected load time and the load residence time through the single-column loading capacity;

Step 3, using the linear relationship between the interconnected load time and the load residence time obtained in Step 2 to solve for the optimal number of operating columns for capturing proteins by MCC under the set loading protein concentration and the protein breakthrough percentage;

Step 4, using the linear relationship between the interconnected load time and the load residence time obtained in Step 2 to solve for the optimal load residence time for capturing proteins by MMC under the set loading protein concentration, the protein breakthrough percentage, and the optimal number of operating columns;

Step 5, using the optimal load residence time obtained in step 4 to solve for the maximum productivity for capturing proteins by MMC.

Preferably, integrating the breakthrough curve to obtain the single-column loading capacity of continuous chromatography in step 2 is specifically:

$$A = \frac{\int_{t=0}^{t_{1\_s}} [c_{exp} - c(t)]dt}{RT_C}$$

In the formula, s is the set breakthrough percentage for the target protein, A (g/L) is the single-column loading capacity of continuous chromatography obtained by integrating the breakthrough curve under the set breakthrough percentage s, t is the loading time, $t_{1\_s}$ (min) is the loading time until reaching the set breakthrough percentage s, $c_{exp}$ (g/L) is the loading protein concentration, c(t) (g/L) is the breakthrough protein concentration, and $RT_C$ (min) is the single-column residence time of the interconnected load of continuous chromatography.

Preferably, establishing the linear relationship between the interconnected load time and the load residence time through the single-column loading capacity in step 2 further includes the following step:

substituting the single-column loading capacity obtained in Step 2 into the formula $$t_C = \frac{A \times RT_C}{c_{exp}} - t_{CW},$$

where $t_C$ (min) is the interconnected load time of continuous chromatography, $RT_C$ (min) is the single-column residence time of the interconnected load of continuous chromatography, A (g/L) is the single-column loading capacity of continuous chromatography obtained in Step 2 by integrating the breakthrough curve under the set breakthrough percentage for the target protein (greater than 50%), $t_{CW}$ (min) is the interconnected wash time of MCC, and $c_{exp}$ (g/L) is the loading protein concentration. Through the above formula, the linear relationship between the interconnected load time $t_C$ and the load residence time $RT_C$ can be obtained.

Preferably, solving for the optimal number of operating columns in Step 3 further includes the following steps:

drawing the line $t_C$-$RT_C$ in the t-RT coordinate system based on the linear relationship between the interconnected load time $t_C$ and the load residence time $RT_C$ obtained in Step 2 and drawing the line $$t = \frac{t_{RR} - (N-3)t_{CW}}{(N-2)}$$

in the same coordinate system, where $t_{CW}$ (min) is the interconnected wash time of MCC process, $t_{RR}$ (min) is the R-R time of MCC process and includes the sum of washing time, elution time, and regeneration time, and N is the number of operating columns. By adjusting the N value, the intersection of two lines is changed so that it is within the set residence time range. If only one N value meets the above conditions, then the N value is the optimal number of operating columns for capturing proteins by MCC under the set loading protein concentration and the protein breakthrough percentage. If two or more N values meet the above conditions, the largest N value is selected as the optimal number of operating columns.

Preferably, solving the optimal load residence time in Step 4 further includes the following step:

solving simultaneous equations of the linear relationship equation $$t_C = \frac{A \times RT_C}{c_{exp}} - t_{CW}$$

between the interconnected load time $t_C$ and the load residence time $RT_C$ obtained in Step 2 and the equation $$t_C = \frac{t_{RR} - (N-3)t_{CW}}{(N-2)}$$

to obtain the optimal load residence time, where $t_C$ (min) is the interconnected load time of continuous chromatography, $t_{CW}$ (min) is the interconnected wash time of continuous chromatography, $t_{RR}$ (min) is the R-R time of continuous chromatography and includes the sum of washing time, elution time, and regeneration time, $c_{exp}$ (g/L) is the loading protein concentration, and N is the number of operating columns. The optimal load residence time for capturing proteins by MCC under the set loading protein concentration, the protein breakthrough percentage, and the optimal number of operating columns can be obtained by solving the above two equations simultaneously.

Preferably, solving the optimal load residence time in Step 4 further includes the following graphic methods:

drawing the line $t_C$-$RT_C$ in the t-RT coordinate system based on the linear relationship between the interconnected load time $t_C$ and the load residence time $RT_C$ obtained in Step 2 and drawing the line $$t = \frac{t_{RR} - (N-3)t_{CW}}{(N-2)}$$

in the same coordinate system, where $t_{CW}$ (min) is the interconnected wash time of the continuous chromatography process, $t_{RR}$ (min) is the R-R time of the continuous chromatography process and includes the sum of washing time, elution time, and regeneration time, and N is the number of operating columns. The load residence time corresponding to the intersection of the above two lines is the optimal load residence time for capturing proteins by MCC under the set loading protein concentration, the protein breakthrough percentage, and the optimal number of operating columns.

Preferably, solving the maximum productivity further includes the following step:

substituting the optimal load residence time obtained in Step 4 into the formula $$P_{C,opt} = \frac{c_{exp}}{N \times RT_{C,opt}},$$

where $P_{C,opt}$ (g/L/h) is the maximum productivity under the optimal load residence time, $RT_{C,opt}$ is the optimal load residence time obtained in Step 4, $c_{exp}$ (g/L) is the loading protein concentration, and N is the number of operating columns. The maximum productivity of capturing proteins by MCC can be solved by the above formula.

The present invention has the following advantages:

(1) The linear relationship between the interconnected load time and the load residence time can be used to predict the effects of MCC with different load residence times through the data of a single time of protein breakthrough experiment, which reduces a large number of protein breakthrough experiments and continuous chromatography experiments in the optimization of MCC process, saves human resources, material resources, and experimental costs, and improves the efficiency of process optimization.

(2) The linear relationship between the interconnected load time and the load residence time is found based on a large number of experiments and systematic model analysis. Using this linear relationship instead of a physical model and experiments can simplify the optimization steps, accelerate the optimization speed, and reduce the optimization difficulty while ensuring accuracy, which is helpful for the equipment selection and the estimation of operating parameters in the early stage of process development.

(3) The optimization method proposed in the present invention is versatile and suitable for protein capture by MCC with three or more columns. According to different operation modes, the optimization of MCC processes with three or more columns can realize the comprehensive analysis for different column numbers and the systemic optimization of the continuous process for protein capture.

DETAILED DESCRIPTION OF THE EMBODIMENTS

The technical solutions of the present invention will be clearly and completely described below in combination with the embodiments and drawings of the present invention. Obviously, the embodiments described are part of the embodiments of the present invention, rather than all embodiments. Based on the embodiments of the present invention, all other embodiments obtained by those having ordinary skill in the art without creative labor are within the scope of protection of the present invention.

The present invention provides an optimization method for capturing proteins by MCC, where the MCC is used for protein capture, and the number of columns is greater than or equal to 3. The optimization method includes the following steps:

Step 1: Under the conditions of a set loading protein concentration and an arbitrary load residence time, a single protein breakthrough experiment is performed to obtain a protein breakthrough curve.

Step 2: Under a set breakthrough percentage (greater than or equal to 50%), the breakthrough curve is integrated to obtain a single-column loading capacity of MCC, and a linear relationship between the interconnected load time and the load residence time is established through the single-column loading capacity.

Step 3: The optimal number of operating columns for capturing proteins by MCC under the set loading protein concentration and the protein breakthrough percentage is solved based on the linear relationship between the interconnected load time and the load residence time obtained in step 2.

Step 4: The optimal load residence time for capturing proteins by MCC under the set loading protein concentration, the protein breakthrough percentage, and the optimal number of operating columns is solved based on the linear relationship between the interconnected load time and the load residence time obtained in step 2.

Step 5: The maximum productivity of capturing proteins by MCC is solved based on the optimal load residence time obtained in step 4.

After obtaining the above optimal parameters, the present invention adopts MPCC for protein capture according to the obtained optimal parameters. In a separation cycle, each column completes all steps of the continuous chromatography operation and returns to its initial state.

Figure 1:
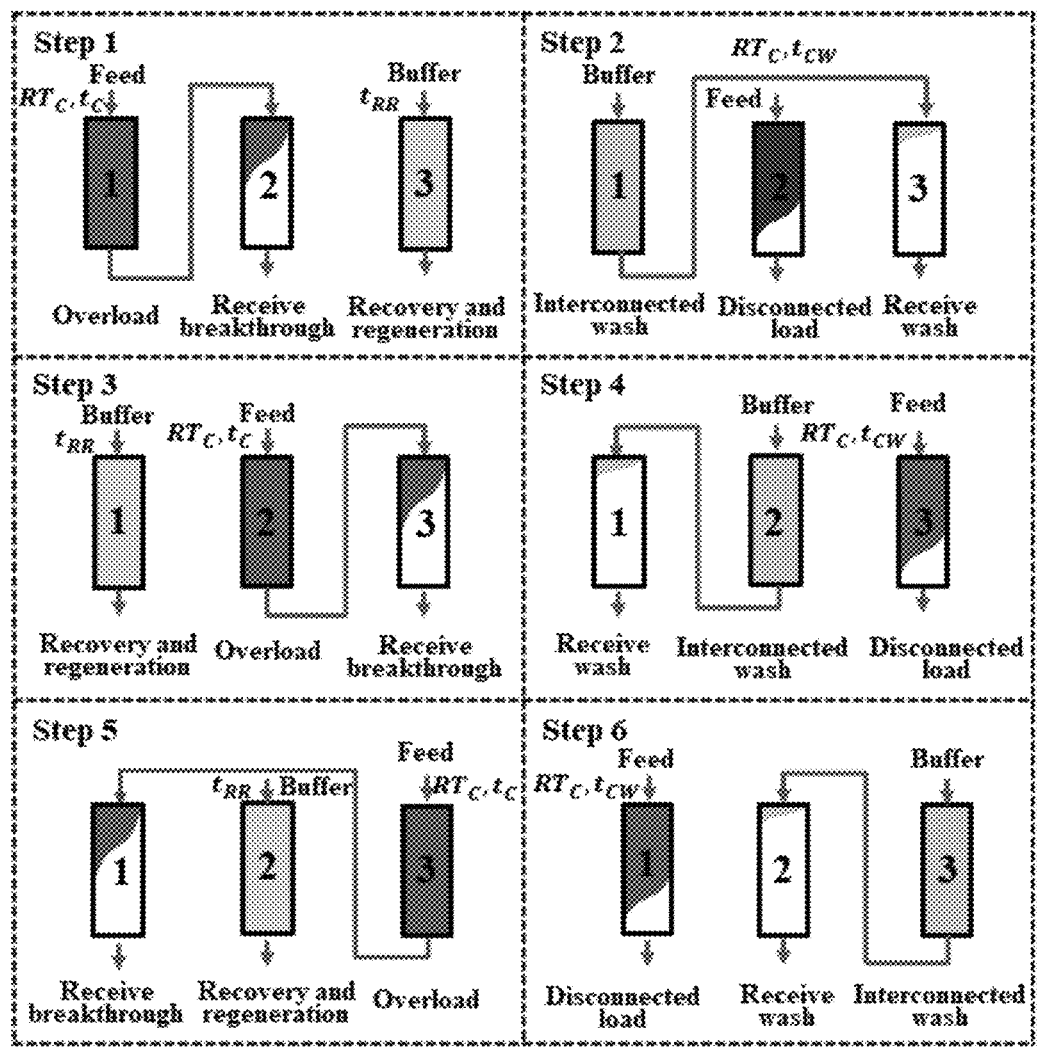
FIG. 1 is a schematic diagram of the operation mode of capturing proteins by a three-column continuous chromatography.
Figure 2:
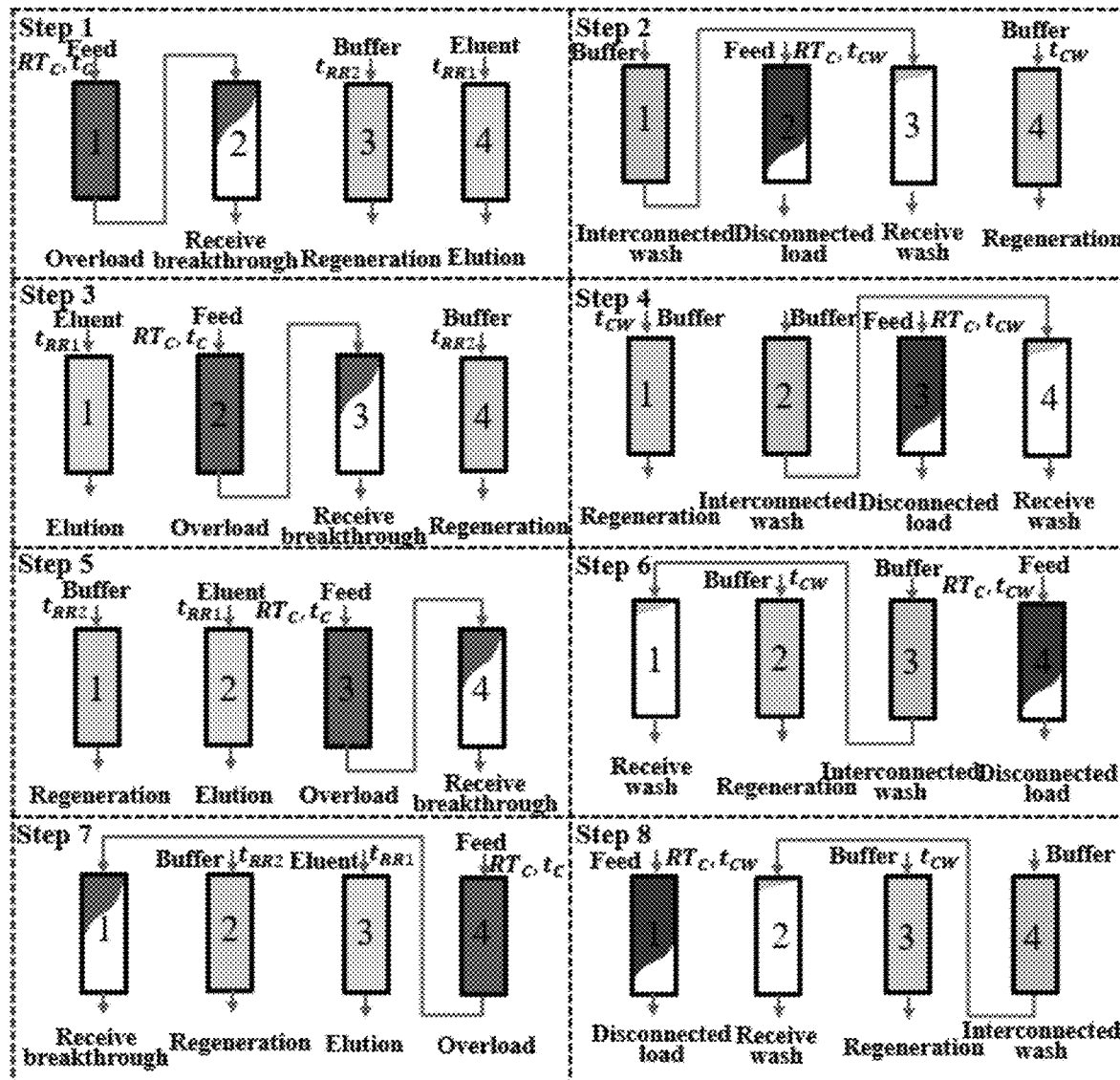
FIG. 2 is a schematic diagram of the operation mode of capturing proteins by a four-column continuous chromatography.
Figure 3:
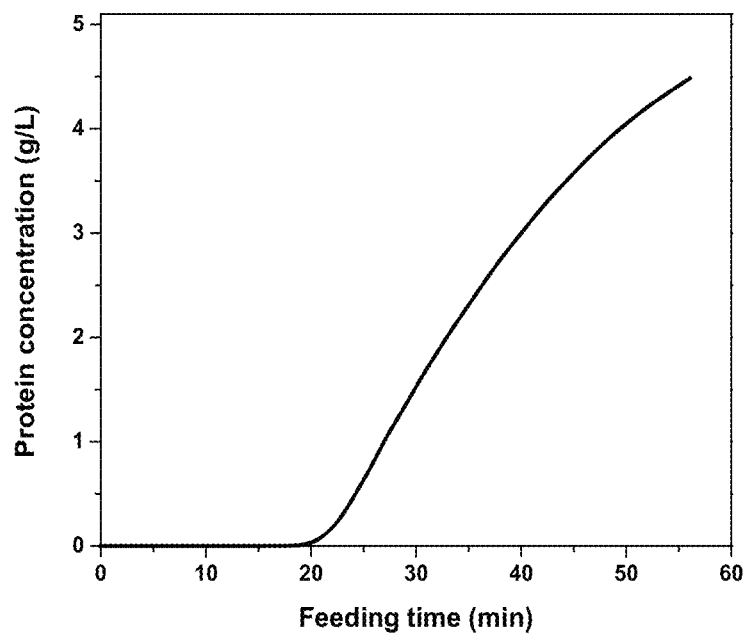
FIG. 3 shows a breakthrough curve obtained when the Praesto® Jetted A50 resin is used at the loading protein concentration of 5 g/L and the load residence time of 2 min.

Embodiment 1. The Solution of the Optimal Number of Operating Columns (1) The Breakthrough Curve Obtained by Experiments The Praesto Jetted® A50 resin from Purolite company is used to pack a 5 ml chromatographic column. The immunoglobulin G with a concentration of 5 g/L is used for loading, and the load residence time is 2 min. The breakthrough experiment is conducted, and the loading is stopped when the breakthrough protein concentration reaches 4.5 g/L. The breakthrough curve is shown in FIG. 3.

(2) The Establishment of the Linear Relationship between the Interconnected Load Time and the Load Residence Time When the set breakthrough percentage is 0.5 (that is, 50% breakthrough), the breakthrough curve is integrated to obtain the single-column loading capacity of 79.8 g/L. The R-R time $t_{RR}$ is 55 min and the interconnected wash time $t_{CW}$ is 8 min after optimization by conventional batch chromatography experiment. The above single-column loading capacity, etc., is substituted into the following formula, and the linear relationship between the interconnected load time $t_C$ and the load residence time $RT_C$ can be written as follows:

$$t_C = \frac{A \times RT_C}{c_{exp}} - t_{CW} = 15.9 RT_C - 8$$

(3) The Solution of the Optimal Number of Operating Columns

Figure 4:
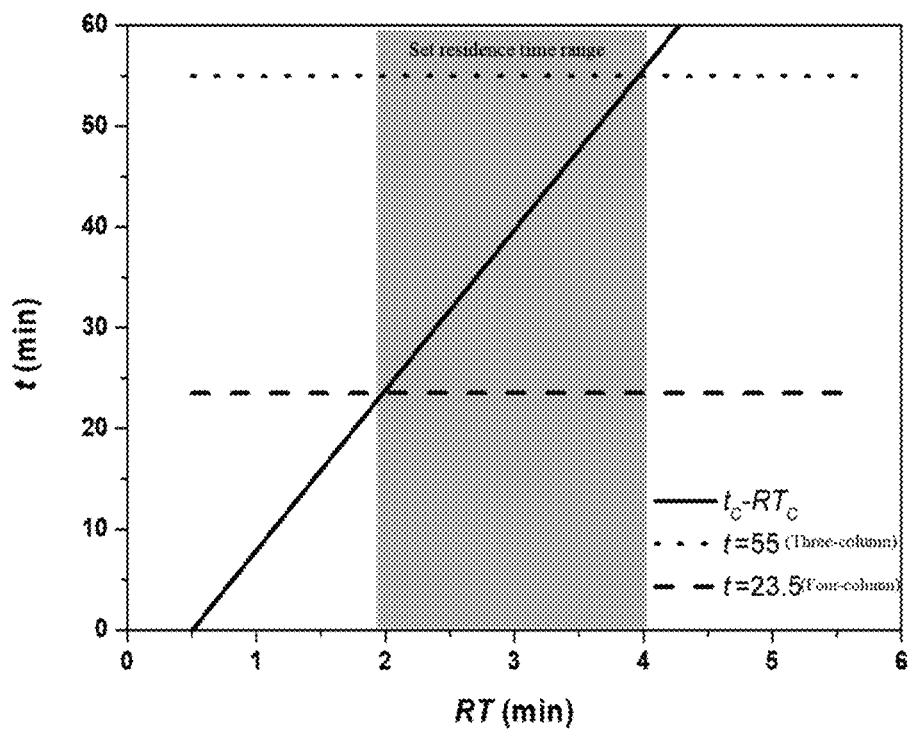
FIG. 4 shows a solving method of the optimal number of operating columns when the Praesto® Jetted A50 resin is used at the loading protein concentration of 5 g/L.

According to the above linear relationship equation, the line $t_C$ -$RT_C$ is drawn in the t-RT coordinate system, as shown in FIG. 4.

According to the linear equation of $$t = \frac{t_{RR} - (N-3)t_{CW}}{(N-2)},$$

when the number of columns N equals 3, then $$t = \frac{55 - (3-3) \times 8}{(3-2)} = 55 (\text{min})$$

In the t-RT coordinate system, line t=55 is drawn.

As shown in FIG. 4, the $RT_C$ of the intersection of $t_C$ -$RT_C$ and t=55 is 3.9 min. Generally, it is recommended that the single-column residence time in the interconnected load stage of MCC is 2 min-4 min, and this $RT_C$ is within this range. Therefore, this system is suitable for three-column continuous chromatography.

Let the number of columns N=4, there is:

$$t = \frac{55 - (4-3) \times 8}{(4-2)} = 23.5 (\text{min})$$

In the t-RT coordinate system, line t=23.5 is drawn.

As shown in FIG. 4, the $RT_C$ of the intersection of $t_C$ -$RT_C$ and t=23.5 is 2 min, which is within the recommended load residence time range. Therefore, this system is suitable for the four-column MCC. Since the system applies to both the three-column system and the four-column system, the four-column system with more columns is selected to be the optimal operating system.

Under the conditions of the protein concentration being 5 g/L and the protein breakthrough percentage being 0.5, the three-column, four-column, and five-column MCC experiments are performed with the Praesto® Jetted A50 resin. The maximum productivity of the three modes is 25.6 g/L (the load residence time is 3.9 min), 37.5 g/L (the load residence time is 2 min), and 30 g/L (the load residence time is 2 min), respectively. Specifically, the four-column continuous chromatography has the maximum productivity, which is consistent with the optimization results, so the optimal number of operating columns is verified to be 4.

Figure 5:
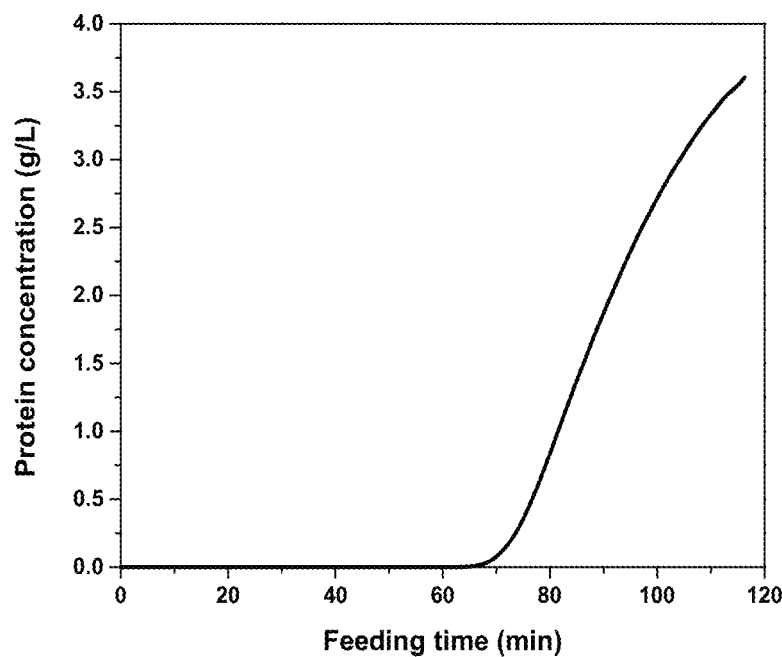
FIG. 5 shows a breakthrough curve obtained when the Praesto® Jetted A50 resin is used at the loading protein concentration of 4 g/L and the load residence time of 4 min.

Embodiment 2. The Solution of the Optimal Load Residence Time (1) The Breakthrough Curve Obtained by Experiments The Praesto® Jetted A50 resin from Purolite company is used to pack a 5 ml chromatographic column. The immunoglobulin G with a concentration of 4 g/L is used for loading, and the load residence time is 4 min. The breakthrough experiment is conducted, and the loading is stopped when the breakthrough protein concentration reaches 3.6 g/L. The breakthrough curve is shown in FIG. 5.

(2) The Establishment of the Linear Relationship between the Interconnected Load Time and the Load Residence Time When the set breakthrough percentage is 0.7 (that is, 70% breakthrough), the breakthrough curve is integrated to obtain the single-column loading capacity of 90.1 g/L. The R-R time $t_{RR}$ is 55 min and the interconnected wash time $t_{CW}$ is 8 min after optimization by conventional batch chromatography experiment. The above single-column loading capacity, etc., is substituted into the following formula, and the linear relationship between the interconnected load time $t_C$ and the load residence time $RT_C$ can be written as follows:

$$t_C = \frac{A \times RT_C}{c_{exp}} - t_{CW} = 22.5RT_C - 8$$

(3) The Solution of the Optimal Number of Operating Columns

Figure 6:
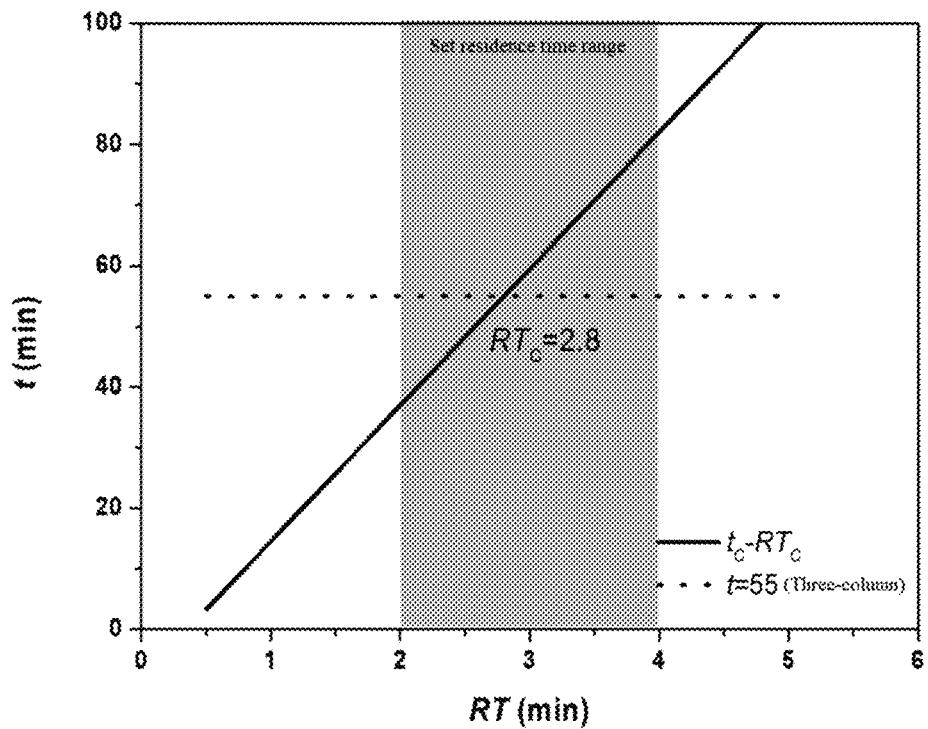
FIG. 6 shows a solving method of the optimal load residence time when the Praesto® Jetted A50 resin is used at the loading protein concentration of 4 g/L.

According to the above linear relationship equation, the line $t_C$ -$RT_C$ is drawn in the t-RT coordinate system, as shown in FIG. 6.

According to the linear equation $$t = \frac{t_{RR} - (N-3)t_{CW}}{(N-2)},$$

when the number of columns N equals 3, then $$t = \frac{55 - (3-3) \times 8}{(3-2)} = 55 \text{(min)}$$

In the t-RT coordinate system, line t=55 is drawn.

As shown in FIG. 6, the $RT_C$ of the intersection of $t_C$-$RT_C$ and t=55 is 2.8 min. Generally, it is recommended that the single-column residence time in the interconnected load stage of MCC is 2 min-4 min, and this $RT_C$ is within this range. Therefore, the optimal number of operating columns is 3, that is, the three-column continuous chromatography.

(4) The Solution of the Optimal Load Residence Time by Simultaneous Equation Method The two linear equations mentioned above are simultaneously solved:

$$\begin{cases} t_C = 22.5RT_C - 8 \\ t_C = 55 \end{cases}$$

The optimal load residence time $RT_{C,opt}$ is solved and determined to be 2.8 min.

(5) The Solution of the Optimal Load Residence Time by Graphic Method

According to the equation of the linear relationship between the interconnected load time $t_C$ and the load residence time $RT_C$ mentioned above, the line $t_C$ -$RT_C$ is drawn in the t-RT coordinate system, as shown in FIG. 6.

According to the linear equation $$t = \frac{t_{RR} - (N-3)t_{CW}}{(N-2)},$$

when the number of columns N=3, then t=55 min. In the t-RT coordinate system, the line t=55 is drawn.

The abscissa corresponding to the intersection of the above two lines is the optimal load residence time, which is 2.8 min obtained from FIG. 6.

Under the conditions of the protein concentration being 4 g/L and the protein breakthrough percentage being 0.7, the three-column MCC experiment is performed with the Praesto® Jetted A50 resin in the load residence time range of 2 min-4 min. The experimental results show that only when the load residence time is 2.8 min, the interconnected load time $t_C$ and the R-R time $t_{RR}$ are basically equal, and the waiting time is close to 0 min. In this case, the productivity of MCC is 27.6 g/L/h, which is higher than that under other load residence times and is consistent with the optimization results.

Embodiment 3. The Solution for the Maximum Productivity

The optimal load residence time obtained in Embodiment 2 is substituted into the following formula:

$$P_{C,opt} = \frac{c_{exp}}{N \times RT_{C,opt}} = \frac{4}{3 \times 2.8} = 0.476 \text{ g/L/min} = 28.6 \text{ g/L/h}$$

The maximum productivity is obtained to be 28.6 g/L/h.

Under the conditions of the loading protein concentration being 4 g/L, the optimal load residence time being 2.8 min, and the set breakthrough percentage being 0.7, the three-column MCC experiment for protein capture is conducted with the Praesto® Jetted A50 resin. It is found that the loading time $t_C$ and the R-R time $t_{RR}$ are basically equal. At this time, the productivity of MCC is 27.6 g/L/h, which is close to the predicted maximum productivity of 28.6 g/L/h and higher than the productivity under other conditions. The method of the present invention is confirmed to be effective.

Figure 7:
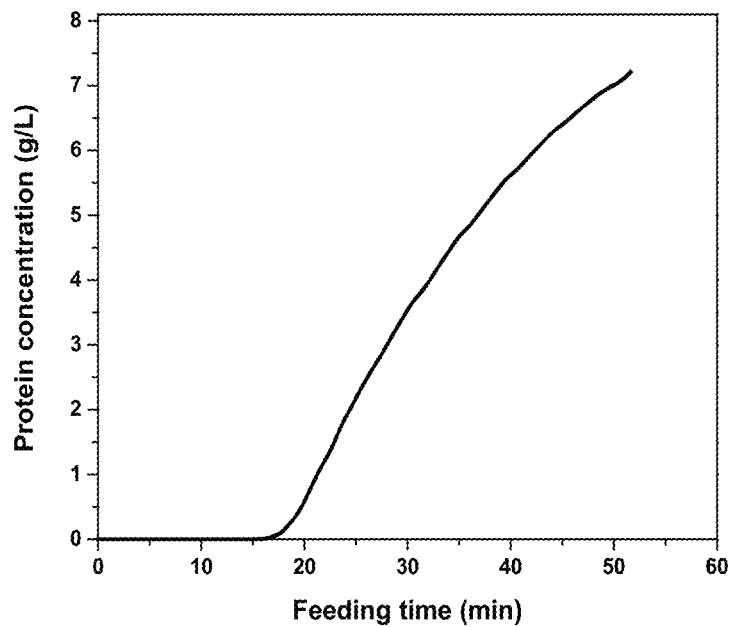
FIG. 7 shows a breakthrough curve obtained when the Mabselect SuRE™ LX resin is used at the loading protein concentration of 8 g/L and the load residence time of 3 min.

Embodiment 4. The Solution of the Optimal Number of Operating Columns (1) The Breakthrough Curve Obtained by Experiments The Mabselect™ SuRE LX resin from GE Healthcare company is used to pack a 10 ml chromatographic column, the concentration of mAb protein is 8 g/L, and the load residence time is 3 min. The breakthrough experiment is conducted, and the loading is stopped when the breakthrough protein concentration reaches 7.2 g/L. The breakthrough curve is shown in FIG. 7.

(2) The Establishment of the Linear Relationship between the Interconnected Load Time and the Load Residence Time When the set breakthrough percentage is 0.75 (that is, 75% breakthrough), the breakthrough curve is integrated to obtain the single-column loading capacity of 85.1 g/L. The R-R time $t_{RR}$ is 43.75 min and the interconnected wash time $t_{CW}$ is 6 min after conventional batch chromatography optimization experiment. The above single-column loading capacity, etc., is substituted into the following formula, and the linear relationship between the interconnected load time $t_C$ and the load residence time $RT_C$ can be written as follows:

$$t_C = \frac{A \times RT_C}{c_{exp}} - t_{CW} = 10.6RT_C - 6$$

(3) The Solution of the Optimal Number of Operating Columns

Figure 8:
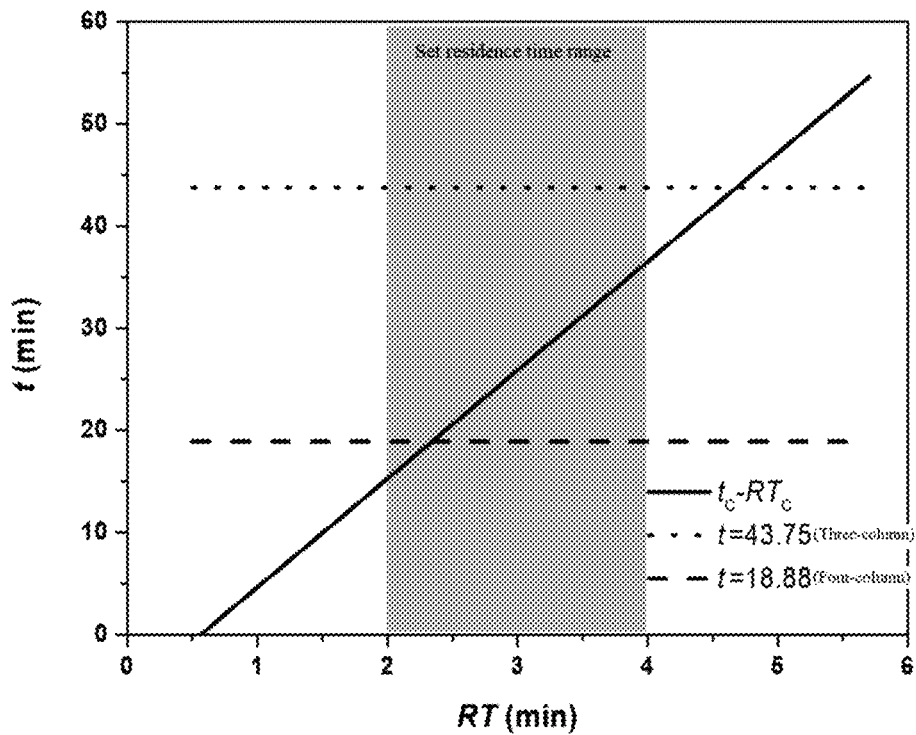
FIG. 8 shows a solving method of the optimal number of operating columns when the Mabselect SuRE™ LX resin is used at the loading protein concentration of 8 g/L.

According to the above linear relationship equation, the line $t_C$ -$RT_C$ is drawn in the t-RT coordinate system, as shown in FIG. 8.

According to the linear equation $$t = \frac{t_{RR} - (N-3)t_{CW}}{(N-2)},$$

when the number of columns N equals 3, then $$t = \frac{43.75 - (3-3) \times 6}{(3-2)} = 43.75(\text{min})$$

In the t-RT coordinate system, the line t=43.75 is drawn.

As shown in FIG. 8, the $RT_C$ of the intersection of $t_C$-$RT_C$ and t=43.75 is 4.7 min. Generally, it is recommended that the single-column residence time in the interconnected load stage of continuous chromatography is 2 min-4 min, and this $RT_C$ is not within this range and is not suitable for the three-column MCC.

Let the number of columns be N=4, then $$t = \frac{43.75 - (4-3) \times 6}{(4-2)} = 18.88(\text{min})$$

In the t-RT coordinate system, the line t=18.88 is drawn.

As shown in FIG. 8, the $RT_C$ of the intersection of $t_C$-$RT_C$ and t=43.75 is 2.3 min, which is within the recommended load residence time range. Therefore, the optimal number of operating columns for this system is 4.

Under the conditions of the protein concentration being 8 g/L and the protein breakthrough percentage being 0.75, the three-column, four-column, and five-column MCC experiments are performed with the Mabselect SuRE™ LX resin. The maximum productivity of the three modes is 34.7 g/L (the load residence time is 4 min), 52.2 g/L (the load residence time is 2.3 min), and 48 g/L (the load residence time is 2 min), respectively. Specifically, the four-column continuous chromatography has the maximum productivity, which is consistent with the optimization results, so the optimal number of operating columns is verified to be 4.

Figure 9:
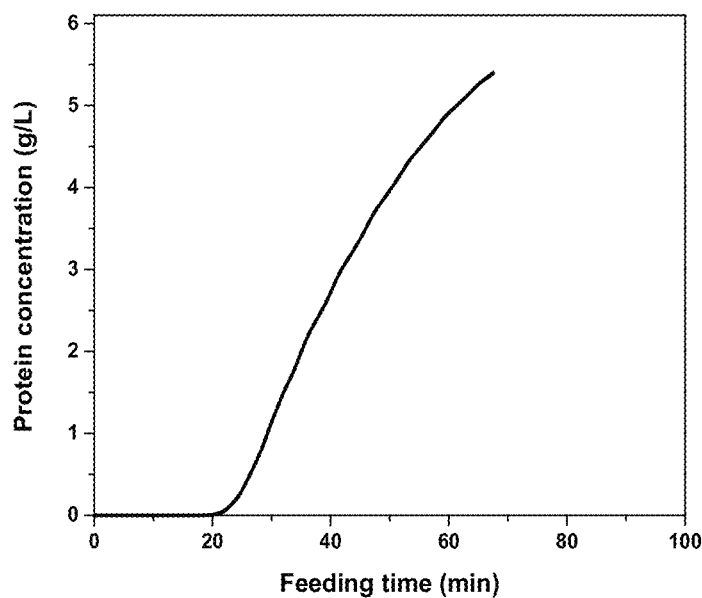
FIG. 9 shows a breakthrough curve obtained when the Mabselect™ SuRE LX resin is used at the loading protein concentration of 6 g/L and the load residence time of 3 min.

Embodiment 5. The Solution of the Optimal Load Residence Time (1) The Breakthrough Curve Obtained by Experiments The Mabselect™ SuRE LX resin from GE Healthcare company is used to pack a 10 ml chromatographic column, the concentration of mAb protein is 6 g/L, and the load residence time is 3 min. The breakthrough experiment is conducted, and the loading is stopped when the breakthrough protein concentration reaches 5.4 g/L. The breakthrough curve is shown in FIG. 9.

(2) The Establishment of the Linear Relationship between the Interconnected Load Time and the Load Residence Time When the set breakthrough percentage is 0.6 (that is, 60% breakthrough), the breakthrough curve is integrated to obtain the single-column loading capacity of 78.3 g/L. The R-R time $t_{RR}$ is 43.75 min and the interconnected wash time $t_{CW}$ is 6 min after optimization by conventional batch chromatography experiment. The above single-column loading capacity, etc., is substituted into the following formula, and the linear relationship between the interconnected load time $t_C$ and the load residence time $RT_C$ can be written as follows:

$$t_C = \frac{A \times RT_C}{c_{exp}} - t_{CW} = 13.1 RT_C - 6$$

(3) The Solution of the Optimal Number of Operating Columns

Figure 10:
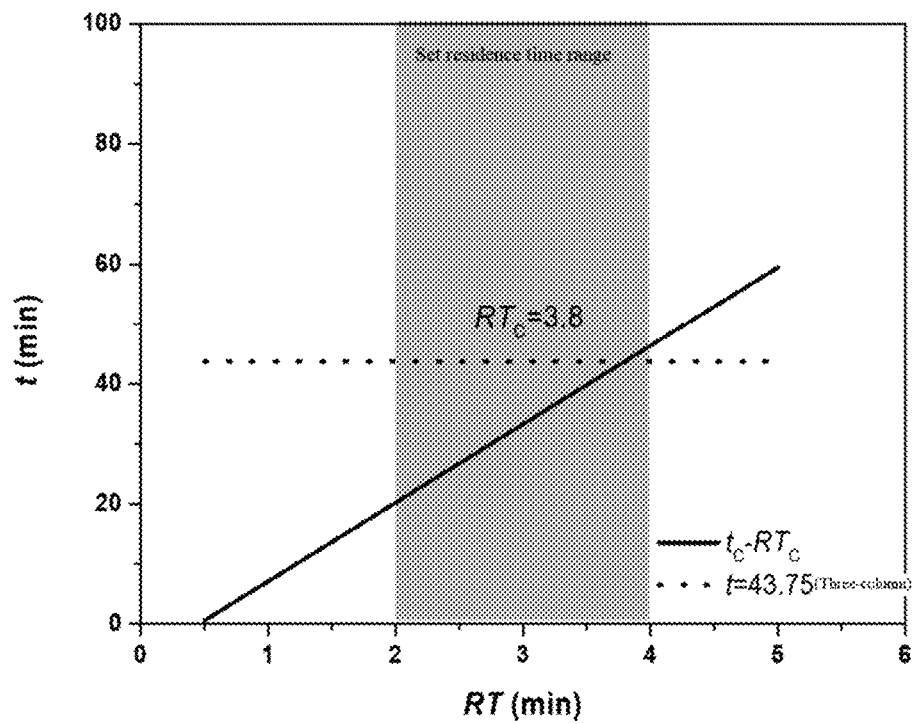
FIG. 10 shows a solving method of the optimal load residence time when the Mabselect SuRE™ LX resin is used at the loading protein concentration of 6 g/L.

According to the above linear relationship equation, the line $t_C$ -$RT_C$ is drawn in the t-RT coordinate system, as shown in FIG. 10.

According to the linear equation $$t = \frac{t_{RR} - (N-3)t_{CW}}{(N-2)},$$

when the number of columns N equals 3, there is:

$$t = \frac{4.375 - (3-3) \times 6}{(3-2)} = 43.75(\text{min})$$

In the t-RT coordinate system, the line t=43.75 is drawn.

As shown in FIG. 10, the $RT_C$ of the intersection of $t_C$ -$RT_C$ and t=43.75 is 3.8 min. Generally, it is recommended that the single-column residence time in the interconnected load stage of continuous chromatography is 2 min-4 min, and this $RT_C$ is within this range. Therefore, the optimal number of operating columns is 3, that is, the three-column continuous chromatography.

(4) The Solution of the Optimal Load Residence Time by Simultaneous Equation Method The two linear equations mentioned above are simultaneously solved:

$$\begin{cases} t_C = 13.1 RT_C - 6 \\ t_C = 43.75 \end{cases}$$

The optimal load residence time $RT_{C,opt}$ is solved to be 3.8min.

(5) The Solution of the Optimal Load Residence Time by Graphic Method

According to the equation of the linear relationship between the interconnected load time $t_C$ and the load residence time $RT_C$ mentioned above, the line $t_C$ -$RT_C$ is drawn in the t-RT coordinate system, as shown in FIG. 10.

According to the linear equation $$t = \frac{t_{RR} - (N-3)t_{CW}}{(N-2)},$$

when the number of columns N=3, then t=43.75 min. In the t-RT coordinate system, the line t=43.75 is drawn.

The abscissa corresponding to the intersection of the above two lines is the optimal load residence time, which is 3.8 min obtained from FIG. 10.

Under the conditions of the protein concentration being 6 g/L and the protein breakthrough percentage being 0.6, the three-column MCC experiment is performed with the Mabselect™ SuRE LX resin in the load residence time range of 2 min-4 min. The experimental results show that when the load residence time is 3.8 min, the interconnected load time $t_C$ and the R-R time $t_{RR}$ are basically equal, and the waiting time is close to 0 min. In this case, the productivity of MCC is 30.3 g/L/h, which is higher than that under other load residence times and is consistent with the optimization results.

Embodiment 6. The Solution for the Maximum Productivity

The optimal load residence time obtained in Embodiment 5 is substituted into the following formula:

$$P_{C,opt} = \frac{c_{exp}}{N \times RT_{C,opt}} = \frac{6}{3 \times 3.8} = 0.526 \text{ g/L/min} = 31.6 \text{ g/L/h}$$

The maximum productivity is obtained to be 31.6 g/L/h.

Under the conditions of the loading protein concentration being 6 g/L, the optimal load residence time being 3.8 min, and the set breakthrough percentage being 0.6, the three-column MCC experiment for protein capture is conducted with the Mabselect™ SuRE LX resin. It is found that the loading time $t_C$ and the R-R time $t_{RR}$ are basically equal. At this time, the productivity of MCC is 30.3 g/L/h, which is close to the predicted maximum productivity of 31.6 g/L/h and higher than the productivity under other conditions. The method of the present invention is confirmed to be effective.

It should be understood that the exemplary embodiments described herein are illustrative and not restrictive. Although one or more embodiments of the present invention are described in conjunction with the drawings, it should be understood by those of ordinary skill in the art that variations of various forms and details may be made without departing from the spirit and scope of the present invention defined by the claims.

What is claimed is:

1. An optimization method for capturing proteins by a multi-column continuous chromatography (MCC), wherein the MCC is used for a protein capture, and a number of columns is greater than or equal to 3, the optimization method comprises the following steps:

step 0, loading a target protein containing solution into a chromatographic column of the MCC for continuous capture, wherein the target protein is a monoclonal antibody and the chromatographic column of the MCC comprises a protein A affinity resin;

step 1, under conditions of a set loading protein concentration and an arbitrary load residence time, performing a single time of a protein breakthrough experiment to obtain a protein breakthrough curve;

step 2, under a set breakthrough percentage for a target protein, integrating the protein breakthrough curve to obtain a single-column loading capacity of the MCC as a first formula:

$$A = \frac{\int_{t=0}^{t_{1\_s}} [c_{exp} - c(t)]dt}{RT_C} - c_{exp} \times s$$

in the first formula, s is the set breakthrough percentage for the target protein, A (g/L) is the single-column loading capacity of the MCC obtained by integrating the protein breakthrough curve at the set breakthrough percentage s, t is a loading time, $t_{1\_s}$ (min) is a loading time until reaching the set breakthrough percentage s, and $c_{exp}$ (g/L) is a loading protein concentration; c(t) (g/L) is a breakthrough protein concentration, and $RT_C$ (min) is a single-column residence time of an interconnected load of the MCC;

establishing a linear relationship between an interconnected load time $t_C$ and a load residence time $RT_C$ through the single-column loading capacity further comprises the following step:

substituting the single-column loading capacity obtained in step 2 into a second formula $$t_C = \frac{A \times RT_C}{c_{exp}} - t_{CW},$$

wherein $t_C$ (min) is the interconnected load time of the MCC, $RT_C$ (min) is the single-column residence time of the interconnected load of the MCC, A (g/L) is the single-column loading capacity of the MCC obtained in step 2 by integrating the protein breakthrough curve at the set breakthrough percentage for the targe protein, $t_{CW}$ (min) is an interconnected wash time of the MCC, and $c_{exp}$ (g/L) is the loading protein concentration; through the first formula and the second formula, the linear relationship between the interconnected load time tc and the load residence time $RT_C$ is obtained;

step 3, solving an optimal number of operating columns for capturing the proteins by the MCC under the set loading protein concentration and a set protein breakthrough percentage based on the linear relationship between the interconnected load time $t_C$ and the load residence time $RT_C$ obtained in step 2 further comprises the following steps:

drawing a line $t_C$-$RT_C$ in a t-RT coordinate system based on the linear relationship between the interconnected load time $t_C$ and the load residence time $RT_C$ obtained in step 2, and drawing a line of a third formula $$t = \frac{t_{RR} - (N-3)t_{CW}}{(N-2)}$$

in the t-RT coordinate system, wherein $t_{CW}$ (min) is the interconnected wash time of the MCC, $t_{RR}$ (min) is a recovery and regeneration (R-R) time of the MCC and comprises a sum of a washing time, an elution time, and a regeneration time, and N is a number of the operating columns; by adjusting a N value, an intersection of two lines is changed so that a load residence time corresponding to the intersection is within a set residence time range; if only one N value meets above conditions, then the N value is the optimal number of the operating columns for capturing the proteins by the MCC under the set loading protein concentration and the set protein breakthrough percentage; if two or more N values meet the above conditions, a largest N value is selected as the optimal number of the operating columns;

step 4, solving an optimal load residence time for the capturing proteins by the MCC under the set loading protein concentration, the set protein breakthrough percentage, and the optimal number of the operating columns based on the linear relationship between the interconnected load time $t_C$ and the load residence time $RT_C$ obtained in step 2;

step 5, solving a maximum productivity of capturing the proteins by the MCC based on the optimal load residence time obtained in step 4; and step 6, optimizing the number of operating columns and the load residence time of the MCC based on the maximum productivity obtained in step 5, and continuously capturing the target protein by the MCC having the optimized number of operating columns and load residence time for the target protein.

2. The optimization method for capturing the proteins by the MCC according to claim 1, wherein the set breakthrough percentage for the target protein is greater than or equal to 50%.

3. The optimization method for capturing the proteins by the MCC according to claim 1, wherein solving the optimal load residence time in step 4 comprises the following step:

solving simultaneous equations of the second formula $$t_C = \frac{A \times RT_C}{c_{exp}} - t_{CW}$$

of the linear relationship between the interconnected load time $t_C$ and the load residence time $RT_C$ obtained in step 2 and the third formula $$t = \frac{t_{RR} - (N-3)t_{CW}}{(N-2)}$$

to obtain the optimal load residence time, wherein $t_C$ (min) is the interconnected load time of the MCC, $t_{CW}$ (min) is the interconnected wash time of the MCC, $t_{RR}$ (min) is the R-R time of the MCC and comprises the sum of the washing time, the elution time, and the regeneration time, $c_{exp}$ (g/L) is the loading protein concentration, and N is the number of the operating columns; the optimal load residence time for capturing the proteins by the MCC under the set loading protein concentration, the set protein breakthrough percentage, and the optimal number of the operating columns is obtained by solving the simultaneous equations.

4. The optimization method for capturing the proteins by the MCC according to claim 1, wherein a graphic method used to solve the optimal load residence time in step 4 comprises the following steps:

drawing the line $t_C$-$RT_C$ in the t-RT coordinate system based on the linear relationship between the interconnected load time $t_C$ and the load residence time $RT_C$ obtained in step 2, and drawing the line of the third formula $$t = \frac{t_{RR} - (N-3)t_{CW}}{(N-2)}$$

in the t-RT coordinate system, wherein $t_{CW}$ (min) is the interconnected wash time of the MCC, $t_{RR}$ (min) is the R-R time of the MCC and comprises the sum of the washing time, the elution time, and the regeneration time, and N is the number of the operating columns; the load residence time corresponding to the intersection of the two lines is the optimal load residence time for capturing the proteins by the MCC under the set loading protein concentration, the set protein breakthrough percentage, and the optimal number of the operating columns.

5. The optimization method for capturing the proteins by the MCC according to claim 1, wherein solving the maximum productivity in step 5 comprises the following step:

substituting the optimal load residence time obtained in step 4 into a fourth formula $$P_{C,opt} = \frac{c_{exp}}{N \times RT_{C,opt}},$$

wherein $P_{C,opt}$ (g/L/h) is the maximum productivity under the optimal load residence time, $RT_{C,opt}$ is the optimal load residence time obtained in step 4, $c_{exp}$ (g/L) is the loading protein concentration, and N is the number of the operating columns; the maximum productivity of capturing the proteins by the MCC is solved by the fourth formula.

* * * * *